United States Patent
Richter et al.

(10) Patent No.: US 7,479,135 B2
(45) Date of Patent: Jan. 20, 2009

(54) AUTOMATIC CONVEYOR DRIVEN BY HYDROGELS, PROVIDED WITH AN ADJUSTABLE OUTPUT CHARACTERISTIC FOR CONVEYING A MEDIUM

(75) Inventors: Andreas Richter, Dresden (DE); Christian Klenke, Dresden (DE); Karl-Friedrich Arndt, Merseburg (DE); Gilbert Schiltges, Kirchberg (CH)

(73) Assignee: Disetronic Licensing AG, Burgdorf (CH)

( * ) Notice: Subject to any disclaimer, the term of this patent is extended or adjusted under 35 U.S.C. 154(b) by 382 days.

(21) Appl. No.: 11/180,315

(22) Filed: Jul. 12, 2005

(65) Prior Publication Data
US 2006/0116664 A1 Jun. 1, 2006

Related U.S. Application Data

(63) Continuation of application No. PCT/EP2004/000138, filed on Jan. 12, 2004.

(30) Foreign Application Priority Data
Jan. 13, 2003 (DE) ................. 103 00 896

(51) Int. Cl.
*A61K 9/22* (2006.01)

(52) U.S. Cl. ................................. 604/892.1
(58) Field of Classification Search ............... 604/892.1
See application file for complete search history.

(56) References Cited

U.S. PATENT DOCUMENTS

| 4,474,575 | A | * | 10/1984 | Eckenhoff et al. | .......... 604/131 |
| 5,180,591 | A | | 1/1993 | Magruder et al. | |
| 5,798,114 | A | * | 8/1998 | Elsberry et al. | .............. 424/423 |
| 5,869,078 | A | | 2/1999 | Baudino | |
| 5,938,654 | A | * | 8/1999 | Wong et al. | .............. 604/892.1 |
| 6,132,420 | A | | 10/2000 | Dionne et al. | |

FOREIGN PATENT DOCUMENTS

| GB | 2 347 081 A | 8/2000 |
| WO | WO 94/05354 | 3/1994 |
| WO | WO 94/07562 | 4/1994 |
| WO | WO 97/21457 | 6/1997 |

* cited by examiner

*Primary Examiner*—Kevin C Sirmons
*Assistant Examiner*—Deanna K Hall
(74) *Attorney, Agent, or Firm*—Dorsey & Whitney LLP

(57) ABSTRACT

A device for the dosed output of a substance, the device involving hydrogel-based osmotic drive, wherein output characteristics of the device, including a time profile, may be adjusted by a user. In some embodiments, the device may be used once and, in other embodiments, it may be used several times.

34 Claims, 9 Drawing Sheets

AUTOMATIC CONVEYOR DRIVEN BY HYDROGELS, PROVIDED WITH AN ADJUSTABLE OUTPUT CHARACTERISTIC FOR CONVEYING A MEDIUM

CROSS-REFERENCE TO RELATED APPLICATION(S)

This application is a continuation of International Patent Application No. PCT/EP2004/000138, filed on Jan. 12, 2004, which claims priority to German Application No. 103 00 896.9, filed on Jan. 13, 2003, the contents of both applications are incorporated in their entirety by reference herein.

BACKGROUND

The invention relates to devices and methods for delivering, administering or dispensing substances, including such devices and methods involving osmotic drive. More particularly, it relates to an automatic hydrogel-based extracorporeal fluid conveyor, in particular example for the delivery or output of insulin, which has a simple structure and small dimensions and time and conveying characteristics which can be adjusted by the user. In some embodiments the device or conveyor is intended for a single use and, in other embodiments, it is capable of use more than once.

It is estimated that there are several million people with chronic diseases living today in Germany alone. Of these, several hundred thousand belong to the type of patient who requires constant medication. Such a patient has a continuous basic requirement for one or more active substances. The individually determined basic requirement, which typically may be or is injected subcutaneously with a syringe, is necessary to ensure that the person affected is able to maintain a normal situation. In addition to this basic requirement, a further requirement for administration of active substances exists in some cases.

Using electromechanically, pneumatically or osmotically driven dosing systems or devices for administrating, delivering, conveying or injecting medication on a permanent and continuous basis is known.

WO 93/16740 discloses an electromechanically operated injection pen. It was developed for self-medication with liquid injectable medicaments or auxiliaries. The liquid is expelled by a piston which is coupled to a spindle and which is driven forward by motor force. The disadvantage of these previously known devices lies in their complex structure and the fact that they are dependent on an energy supply by means of a battery.

DE 41 06 624 discloses an osmotically operated injection system for slow and steady injection of medication. The syringe piston is in this case driven forward via salination or osmotic forces. A fluid of higher concentration is diluted, with increase in volume, as a result of osmotic uptake of a fluid of lower concentration. The working pressure thereby generated is used for driving the piston forward. The functionality is impaired by movable protruding parts and by the absence of a mechanism for delaying activation and triggering. No pulsatile operation is possible with this pump.

An osmotically driven, portable extracorporeal infusion pump is likewise disclosed in U.S. Pat. No. 5,672,167. It comprises two storage pouches: the fluid to be conveyed is accommodated in one of them, and the second pouch contains the driving liquid. Salination or osmotic forces from the concentration equilibrium of two liquids are again used for conveying the fluid. The infusion rate is dependent on the properties of the semipermeable membrane lying in between and must therefore be pre-set at the time of production. The pump is activated by a valve or by the destruction of a seal. Pulsatile operation is possible only by using conventional powered and timed pumps.

U.S. Patent application 2001047161 describes an implantable and osmotically operated system for the administration of medicaments. It is used for long-term administration of liquid or soluble medication. The output characteristic is set, at the time of production, by the choice of membrane and by the material properties of the swelling substance. It is not possible for the physician to subsequently adjust the release time and subsequently adapt the conveying characteristics to the demands of the patient.

U.S. Pat. No. 5,340,590 has already disclosed pump systems which, through a combination of several layers of different osmotic and swelling substances, permit pulsatile operation of the pump. The characteristic curve can be adapted to the patient requirements only during production. The pump system does not have its own swelling agent reservoir and is therefore based on moisture being taken up from the surrounding medium. It is therefore designed only as an implant or as a capsule to be ingested. No delayed release or switch-on mechanism is indicated.

In U.S. Pat. No. 5,209,746, the pulsatile operation of an osmotic pump is achieved by structural means such as constrictions or mechanical barriers. The disadvantages of these systems are that the characteristic curve of the pump can be adapted to the patient requirements only at the time of production and the fact that they are limited to intracorporeal use because of the absence of a swelling agent reservoir. No delayed release or switch-on mechanism is indicated.

A delayed release for osmotically operated pumps is disclosed in U.S. Pat. No. 4,976,966. This is achieved by a pump core with a semipermeable membrane and an osmotic drive being pressed out of an impermeable sleeve.

The pressing out is likewise effected by an osmotic drive situated at the bottom of the outer sleeve. The outer sleeve is perforated or of semipermeable design at its base. This delayed release cannot be adjusted by the user and the pump functions only within a moist environment, i.e. when implanted or in the digestive tract.

While they may be well-suited for their intended purpose, the above-mentioned devices have a number of drawbacks. It is true that extracorporeal insulin pumps have very many adjustment functions and individually adaptable program sequences, but they are of very complicated design and are therefore expensive and generally require external power. The described implantable drug delivery systems operating according to the principle of osmotic pumps are of very simple construction. However, a disadvantage of these is the implantation, which is always associated with high costs and risks, and the impossibility of the patient being able to adjust the pump output characteristic. These devices can also only cover the basic requirement of the patient.

SUMMARY

Accordingly, one object of the present invention is to provide automatic extracorporeal pumps which are of simple construction and are inexpensive to produce, operate without external power and provide the possibility of a patient or user being able to adjust the output characteristics. Moreover, the pumps are to be distinguished by low susceptibility to faults.

In one embodiment, the present invention comprises a device for dosed output of a substance, the device involving osmotic drive, the time profile of the substance output being adjustable. Additional advantageous embodiments are set forth herein.

Some of the benefits of the present invention are:

In a number of chronic diseases, it is necessary to administer the medicament subcutaneously at a certain time during the night. The conveyor or delivery device (which may also be referred to as a pump) described herein is applied by the patient in the evening and activated. It then delivers the medicament automatically at the scheduled time, without needing any further action by the patient. A particular case is diabetes mellitus, where there is an increased insulin demand in the early hours of the morning (dawn phenomenon). This increased demand can be covered by the pump with hydrogel actuator in a manner specific to the patient, without having to wake the patient to do so.

The pump of the present inventon, in one of its variants, makes it possible to generate a constant small volumetric flow over a quite long period of time. This is of relevance in certain technical or medical applications. In particular, in patients with type II diabetes, for example, the basic insulin requirement can be covered in this way. In contrast to the sustained-action insulins available on the market, a constant delivery and uptake of insulin is ensured starting from and within certain time intervals.

By virtue of mechanically adjustable pump characteristics, for example the time at which the conveying starts, the characteristic curve, and the volume of medium to be conveyed, a delivery device or pump in accordance with the present invention is able to realize in a simple manner, and without external power, complicated, programmable procedures, as are required, for example, in insulin pump therapy (CSII).

If smart hydrogels are employed, repeated use of a pump or delivery device in accordance with the present invention is possible.

As their actuator, some embodiments of pumps according to the present invention (which may also be referred to as delivery devices or conveyors) use hydrogels which, because of their volume increase as a result of uptake of swelling agent, also count as a special case of osmotic drive. Hydrogels are the solid-body vehicles with the greatest exploitable change in volume and they operate without external power, i.e. they do not require an external supply of energy, for example in the form of electrical quantities. By means of these hydrogel properties, very simple pumps can be produced which, because of their structure, have predetermined output characteristics.

Modern insulin delivery systems should have adjustable output characteristics, in other words, they should be able to be adapted or adjusted individually by physician or patient. This can be done, on the one hand, by modifying the properties of the hydrogel actuator, although this generally entails a complicated operation. On the other hand, the pump behavior can be adjusted by structural or mechanical measures. This possibility affords the advantage of simple operation.

Functionally, three adjustment possibilities of an insulin pump are relevant:
 I. the delay time from pump initiation to the start of conveying of the medicament,
 II. the time within which the medicament is conveyed, including the output amount per unit of time, and
 III. the characteristic curve (constant, pulsatile).

The invention is based, particularly for II and III, on the recognition that the actuator dynamics have to be variable to permit subsequent adjustment of the pump behavior. This can be fixed by the difference in the chemical solvent potential between gel and environment $$\Delta\mu A = \mu A(\text{gel}) - \mu A(\text{environment}).$$

This equation states that the gel increases its volume through uptake of swelling agent until a state of equilibrium is reached.

One possibility of exerting an influence is through the chemical potential of the solvent in the hydrogel $\mu A(\text{gel})$. This is a material-specific parameter which is determined by the chemical composition, crosslinking density, etc. To adjust the actuator dynamics via this parameter, an actuator from a hydrogel with the desired swelling characteristics must be fitted at the actuator site of a pump, which for example can be done in the form of cartridges or tablets or in another suitable form. However, this possibility is associated with a very complicated operating process.

Further possibilities for subsequent adjustment of the swelling kinetics and actuator dynamics are afforded by varying the chemical potential of the solvent in the environment $\mu A(\text{environment})$. This can be done very simply by making the swelling agent available in dosed quantities. Structurally, this is made possible by adjustability of the cross section of the swelling agent delivery line.

Another possibility is for $\mu A(\text{environment})$ to be altered by variation of the swelling agent mixture. This method, however, likewise involves complicated operation.

The potential difference $\Delta\mu A$ between gel and environment can also be influenced by a pressure counteracting the swelling pressure. Such a pressure can be realized structurally by a spring element or by an element which, as a result of friction, generates a force counteracting the swelling process.

Since the swelling process of hydrogels is controlled by diffusion, the actuator dynamics can also be fixed by the dimension and macroscopic structure of the hydrogel actuator. The relaxation time constant determining the swelling process is $$\tau \sim \frac{d^2}{D_{Coop}}.$$

The equation means that, in addition to the cooperative diffusion coefficient describing the swelling agent and hydrogel system, the smallest characteristic dimension of the hydrogel actuator determines its time behavior by a squared proportionality. Therefore, small hydrogel structures are sought for short swelling times, and large hydrogel structures are sought for long swelling times.

To be able to achieve a pulsatile characteristic curve that can be adjusted by the user, the pump drive should be able to be actuated in such a way that, in each case, it realizes the required conveying rates (amount conveyed per unit of time) in a desired chronological sequence. For this purpose, the possibilities of exerting influence which have already been mentioned can be exploited.

Thus, for example, pulsatile characteristic curves can be realized using actuator segments which are coupled in series and each have different swelling properties. In areas where no conveying is to take place, it is possible to use material segments made of materials which dissolve within a defined time under solvent action. After the dissolving process, the next actuator-effective hydrogel segment is activated by swelling agent. One possibility of adjustment lies in the user assembling the actuator from the required segments.

It is also possible for the user to vary the swelling agent mixture, for example by connecting different solvent reservoirs in the desired sequence to the swelling agent reservoir and using the resulting swelling agent mixture to adjust the actuator dynamics to the requirements.

In a further adjustment possibility, it is possible to apply different counteracting forces in the required sequence. If the counteracting forces are applied, for example, by frictional pairings of bores and round bar segments with respectively defined coefficients of friction, the counterforce can be altered by varying the internal diameter (bore diameter) since the external diameter of the round bar segment is constant. The duration of action of the respective counterforce can be fixed by the guide length of the round bar segment in the specific internal diameter.

A further possibility of adjusting the characteristic curve lies in the use of hydraulic transmission mechanisms. By varying the cross section of the actuator chamber in its direction of swelling or action, then, according to the principle of the conservation of energy, both its force action and its travel can be altered.

A pump characteristic curve can also be altered by varying the cross section of the swelling agent delivery line. If the cross section is narrowed, the pump outputs or delivers slowly, and, if it is widened, the actuator can swell more quickly and the pump has a higher output rate. When the delivery of swelling agent is suppressed, the pump function is interrupted. This can also be used as an emergency cut-out function.

The above-described possibilities for adjusting a characteristic curve of a pump or delivery devicecan, of course, also be used in combination.

An adjustable time delay from initiation of the pump to the start of the actual conveying can also be realized by different methods.

Thus, soluble swelling agent barriers can be fitted into the delivery path, and their delay time can be fixed by the material used and by the latter's effective thickness.

As a further adjustment principle of the time delay, an idling travel of the hydrogel actuator can be used. After activation, it first has to expand in a hollow space which is inactive from the actuator point of view, and is thereafter able to act on the reservoir of medicament. The time delay is in this case a function of the idling travel to be completed.

In contrast to implantable hydrogel pumps, the swelling agent is not made available through the pump environment (in the case of implanted pens, the body fluid is used as swelling agent). A swelling agent reservoir thus has to be integrated into the pump. To ensure independence of the pump function from the position of the applicator (i.e. the swelling agent must always be available), the swelling agent reservoir is to be acted upon by an overpressure such that, even in the case of an unfavorable position, a pressure difference is present which drives the swelling agent into the actuator chamber. The hydrostatic overpressure required in the swelling agent reservoir can, for example, be realized by means of a pretensioned elastic covering or by a spring.

Previous hydrogel-based pumps have generally been designed to be disposed of after just one use. To be able to use pumps more than once, the drive mechanism must be able to be reset to its initial state. This is made possible by using smart hydrogels or swellable polymer networks with discontinuous phase transition behavior. These smart hydrogels have the property of reacting with pronounced changes in volume, in their phase transition range, to minor changes in specific environmental parameters. Thus hydrogels with a lower critical solution temperature characteristic are known which are swollen at temperatures below their phase transition temperature and are unswollen at temperatures above their phase transition temperature.

Thus, for example, the homopolymer poly(N-isopropyl acrylamide) has a phase transition temperature of about 33° C. in an aqueous environment. By copolymerization and also by variation of the swelling agent composition, the point of this phase transition can be adjusted almost at random between 5 and 50° C.

For example, in the case of an actuator made from a poly (N-isopryl acrylamide) copolymer with a phase transition temperature of 45° C., a pump user is able not only to sterilize the pump by placing it in a heat sterilizer or into boiling water, but is also able to reset the pump drive mechanism consisting of the smart hydrogel back to the initial or unswollen state, so that the pump can be used again.

The illustrative embodiments and uses described herein are given only as representative examples of many other conceivable possibilities and are not in any way exhaustive.

DETAILED DESCRIPTION

FIGS. 1, 2a and 2b, and 3 illustrate the structure, production, construction details, and manner of use and functioning of the automatic active substance pumps according to the present invention.

Since the pumps are also intended to satisfy aspects of mass production, a modular design with the fewest possible numbers of individual parts is advantageous, because the individual structural groups then simply have to be joined together in the assembly process.

Figure 1:
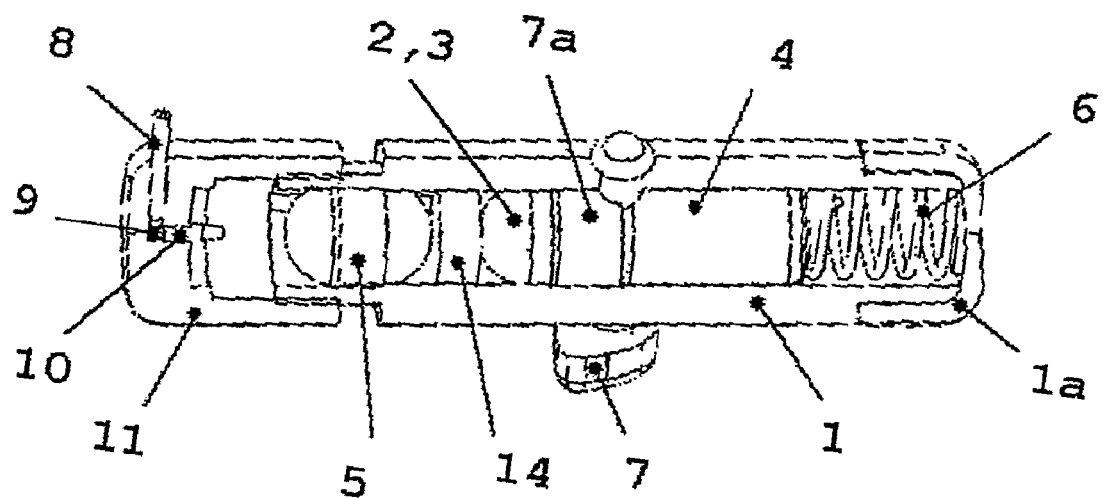
FIG. 1 shows one embodiment of a delivery device in accordance with the present invention, namely, an automatic pump with adjustable time delay from pump initiation to conveying of an active substance, suitable for treatment of dawn phenomenon or for continuous output of active substance over a defined period of time.

The device or pump according to FIG. 1 has a user-adjustable time delay and is designed for treatment of dawn phenomenon. After the time delay has elapsed, it conveys, within a certain period of time, a required amount of active substance. It enables the user, before going to sleep, to set the required delay time and apply and activate the pump. After the set time, the pump automatically conveys the active substance so that the user can sleep through the night. The pump according to FIG. 1 comprises a pump body 1 which in the first instance ensures the mechanical functional reliability and defines the structural space for the other functional elements.

Unlike implantable pumps, an extracorporeal pump cannot draw the swelling agent from its environment in the form of body fluid. The pump therefore contains a swelling agent reservoir 4 in which the swelling agent is kept ready.

To ensure delivery of swelling agent independently of the pump position, the reservoir 4 is acted upon by an overpressure by means of the pretensioning device 6. The hydrostatic overpressure thus generated must be great enough to reliably overcome the gravitational force of the swelling agent and to force the swelling agent at any time into the actuator chamber 3. The swelling agent reservoir can have a fixed, dimensionally stable casing or an elastic covering. A condition of a dimensionally stable casing, whose duty can also be assumed by the pump housing 1, is a movable and sealing stopper via which the overpressure can be coupled into the swelling agent. If a rubber elastic material is used for an elastic covering, for example a shaped part made of latex or silicone, the hydrostatic overpressure for obtaining the position-independent availability of swelling agent can be applied in functional integration by the elastic restoring force of the covering.

To initiate the pump, the pump trigger 7 is activated. In the arrangement shown, it can operate according to two principles. If it is equipped with a destructive element, for example a hook, it destroys the covering of the swelling agent reservoir 4 so that the swelling agent can pass through the swelling agent delivery element 7a into the actuator chamber 3. If it is designed as a shut-off valve, when actuated it establishes a connection between swelling agent reservoir 4 and actuator chamber 3. The swelling agent delivery element 7a has, in addition to its duty as trigger, the role of making the swelling agent available after pump initiation in a defined amount per unit of time to the gel actuator 2. This delivery rate can be fixed structurally via the effective flowable delivery cross section and the extent of the hydrostatic overpressure of the swelling agent reservoir. The delivery cross section can, for example, be fixed by the diameter and the number of bores in the swelling agent delivery element 7a or by the use of porous materials or membranes. Since porous materials or membrane materials with defined permeabilities and low tolerances are commercially available in almost any size, they are ideal for use in the swelling agent delivery element 7a.

After the swelling agent has reached the actuator chamber 3, the actuator material 2 made of a swellable polymer network begins to swell as a result of uptake of swelling agent. On account of the single available degree of freedom, the actuator 2 will now expand in one direction toward the active substance reservoir and delay disk.

The actuator chamber 3 shown in FIG. 1 has a shape-flexible covering, e.g. in the form of latex or polyethylene film material. This stretches in the elastic configuration (e.g. rubber elastic latex covering) according to the increase in volume of the gel or it is filled more and more by this (for example shape-flexible polyethylene film cover). The actuator chamber itself can also have a rigid casing, as is the case if, for example, the actuator chamber walls are formed by the pump housing 1, the fixed swelling agent delivery element 7a and the movable delay disk 14.

The actuator material 2 itself is composed of swellable polymer networks. Commercially available materials appear to be especially suitable, for example those used as superabsorbers. In addition to their low cost, these are distinguished by very good actuator properties, a high degree of volume expansion and good consistency of their properties. The most important actuator materials are polymers based on acrylic acid, e.g. anionic polyacrylates such as Na polyacrylate. Other swellable polymer networks with the required properties can of course also be used. Since this field is very wide, only a small number of derivative classes are listed without any claim to completeness: acrylamides, vinyl alcohols, urethanes, vinyl ethers, cellulose, gelatin.

The actuator material and its macroscopic structure determine the characteristic curve of the pump in conjunction with the available swelling agent, its amount per unit of time, and the forces counteracting the actuator.

Three material parameters are relevant to the actuator properties. First, the chemical composition of the polymer network determines the attainable scope of the actuator properties and the swelling behavior over time. Second, by adjusting the crosslinking conditions via the crosslinking density and the microscopic structure (e.g. homogeneous or porous polymer network), the time profile, the attainable maximum degree of swelling and the possible swelling pressure can likewise be fixed.

The third material parameter for setting the actuator properties is its macroscopic structure. The actuator materials are in most cases filled into the actuator chamber 3 not as whole bodies but instead in particle form. The particle size and the particle size distribution determine the maximum possible actuator stroke, the time profile and the repeat accuracy of the actuator behavior. This effect is caused by the ratio of the total actuator volume to the dry volume of the polymer network. If the effective void space between the individual particles is great, the particles have to use a considerable part of their swelling process to fill these hollow spaces, so that both the maximum possible actuator stroke and also the effective swelling time of the actuator decrease. The particle size distribution, by contrast, influences the repeat accuracy of the actuator behavior. If it is chosen too widely, the time profile and the actuator stroke vary greatly.

The suitable particle sizes and particle size distributions can be obtained very easily by grinding the starting material and then sifting with test screens. Characteristic particle sizes are between approximately 50 μm and 1500 μm, and the particle size distributions should not exceed the limits of approximately ±100 μm.

Figure 3:
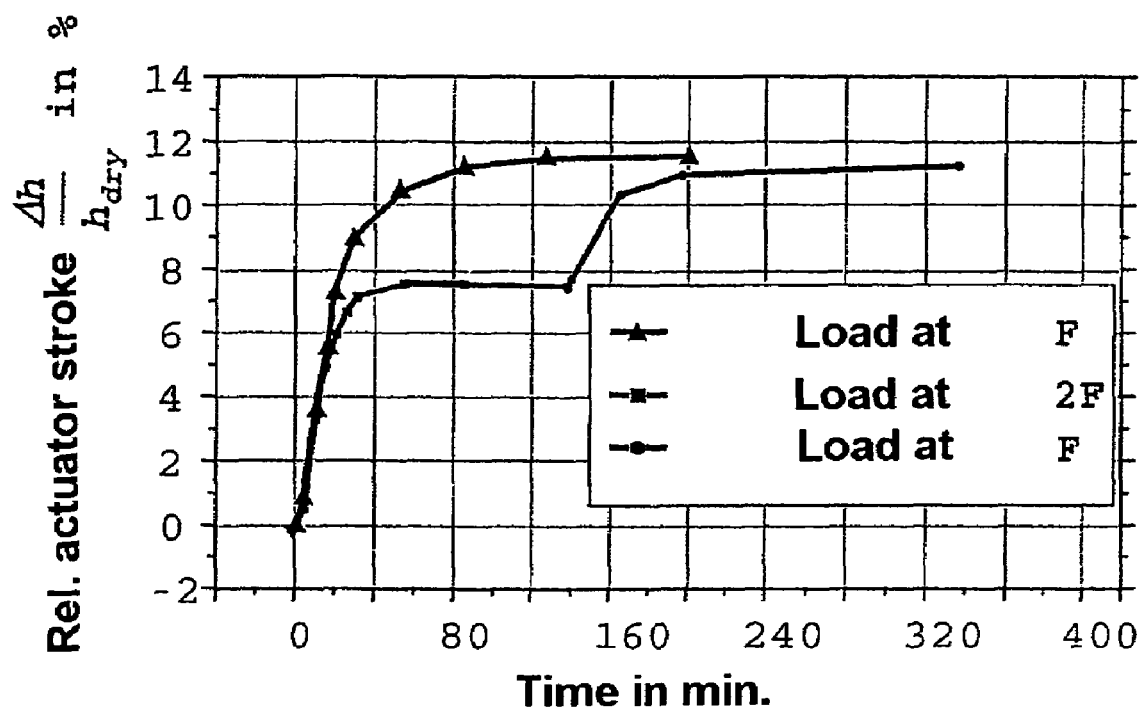
FIG. 3 shows the mode of action of a frictional force acting against a swelling force.

At the start of the unidirectional expansion of the gel actuator 2 as a result of the swelling agent action, it will reach the delay disk 14. This component serves to reduce the structural length of the pump. The mode of function of the delay disk is illustrated in FIG. 3. If the actuator 2 only has to overcome the force F in the swelling process, it will, after a certain time, reach its swelling equilibrium characteristic of F. However, if it works counter to a force of the magnitude 2F, as is present in the case of a friction pairing (press fit or transition fit) of delay disk 14 and pump housing 1, the actuator will reach its swelling equilibrium characteristic of 2F at a smaller actuator stroke for approximately the same time. A subsequent unloading to F, as happens for example when the delay disk 14 moves from the friction or press-fit area into a clearance fit area, effects renewed initiation of the swelling process to the characteristic swelling equilibrium of force F.

Figure 2A:
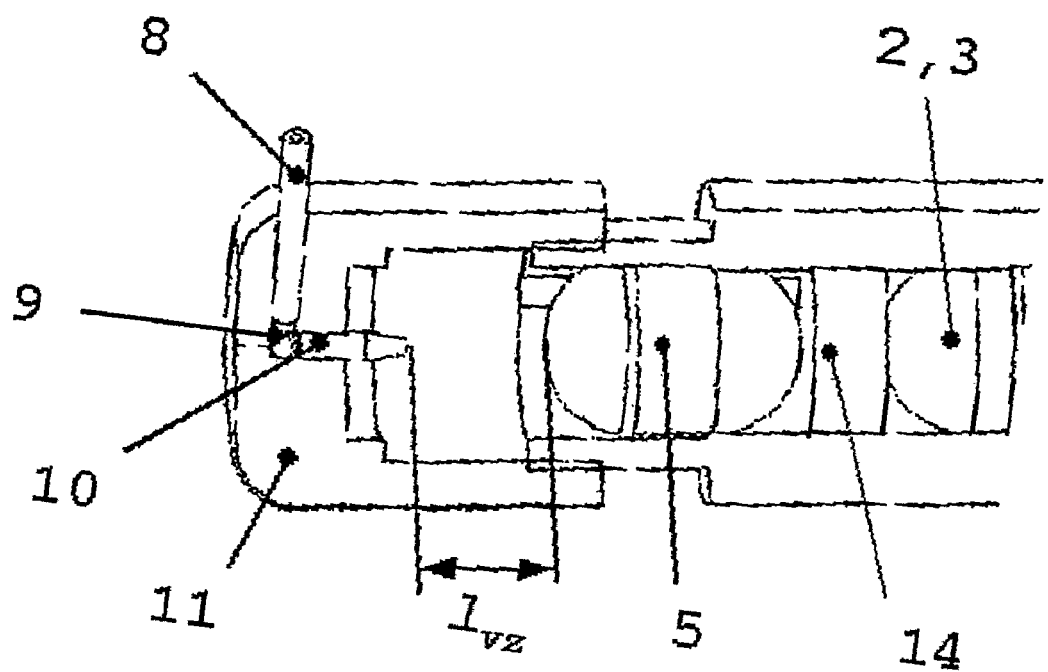
FIG. 2a shows the pump in a starting position (non-activated state)
Figure 2B:
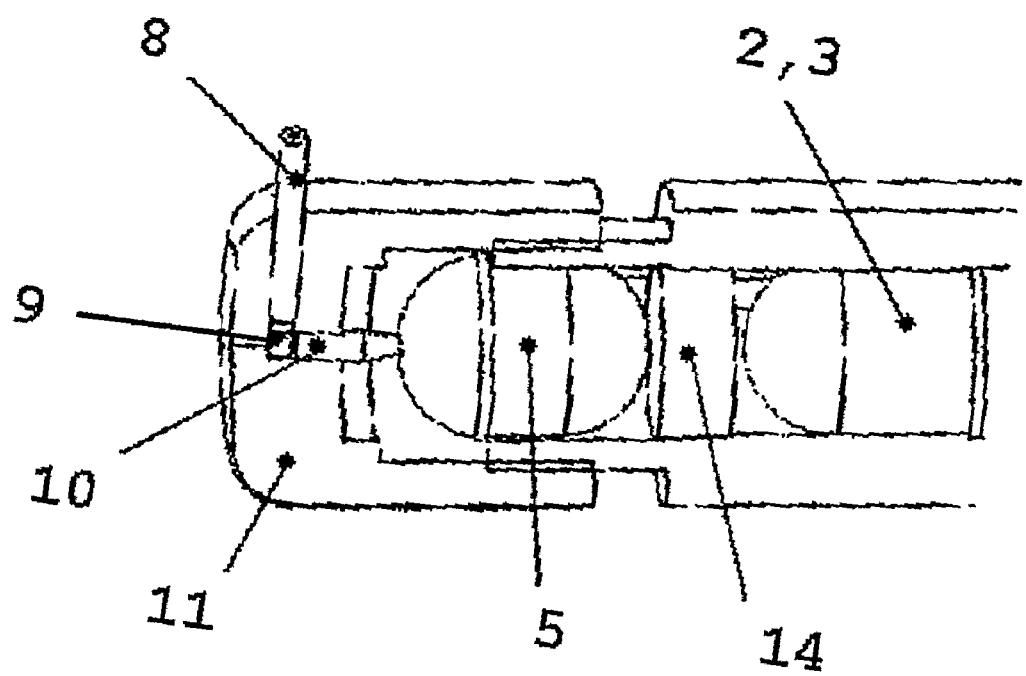
FIG. 2b shows the pump after the delay time has elapsed.

The principle of the time delay between initiation of the pump and the start of conveying of the active substance is illustrated by FIGS. 2a and 2b. FIG. 2a shows the initial state of the pump shortly after activation of the actuator 2. As a result of the actuator swelling, the actuator 2 will now push the delay disk 14, if this is present, and the active substance reservoir 5, if this is movable, in the direction of the opener pin 10 via a length lvz until the end position of the time delay process according to FIG. 2b is reached, where the active substance reservoir 5 is pressed against the opener pin 10.

The time delay is a function of the length lvz. The greater lvz is, the longer the time delay. The pump user can adjust the time delay by changing the length lvz by turning the setting screw 11 which is secured on a thread on the pump housing 1. Other suitable adjustment structures may be used as well. A suitable time scale is advantageously located on the pump housing 1, and a marking is located on the setting screw 11. The relationship between time delay and lvz can be assumed to be linear when the actuator 2 is overdimensioned and thus only the practically linear rise of the actuator curve (see FIG. 3) is used. This relationship is an optimization parameter which has to be adapted experimentally to the particular conveyor task.

After passing the time delay unit, the active substance reservoir 5 which has hitherto been closed in a sterile manner is pressed by the actuator 2 against the opener pin 10 in such a way that the active substance reservoir covering is pierced by the latter and thus opened. With the remaining actuator stroke, the active substance reservoir, which in the case illustrated has an elastic covering, is emptied via the active substance outlet 8 within a certain period of time. In the case of a rigid reservoir design 5, the actuator has a movable member, e.g. a stopper, and the opener pin has a piercable membrane.

If protection against excessive discharge of active substance is required, as may occur for example in mechanical deformation of an elastic pump housing 1, a flow limiter 9 in the form of ball valves (see FIG. 1), flap valves or the like can be easily placed between pin 10 and active substance outlet 8. These valves are controlled by pressure differential. At low pressure differences or flow velocities, they are opened, whereas, if certain pressure differences or flow velocities are exceeded between inlet and outlet, they close.

Figure 4:
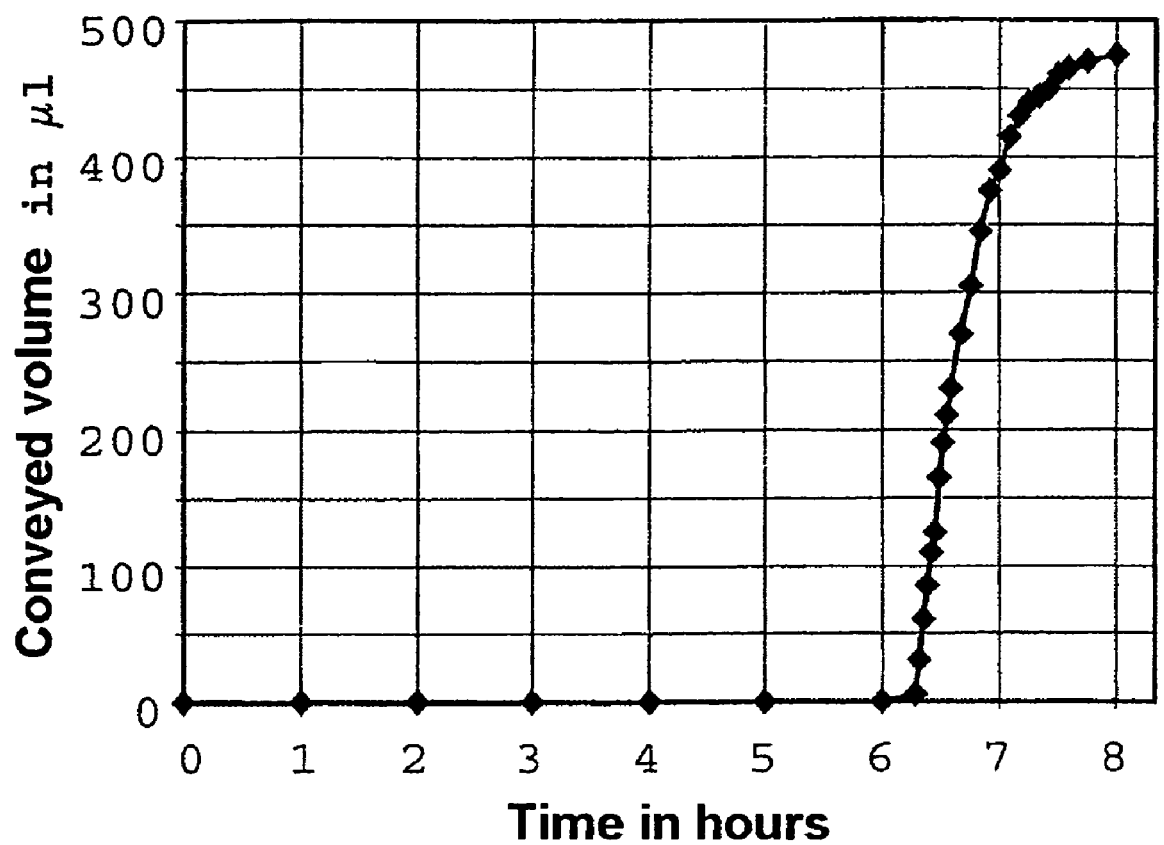
FIG. 4 shows a characteristic curve of the conveying by a pump according to FIG. 1.

FIG. 4 shows an example of use of the pump illustrated in FIG. 1. A user wishes to go to bed at 21.00 h. He has to administer his active substance at 03.00 h. Therefore, he sets a delay time of 6 hours by turning the setting screw 11 accordingly. He then applies the pump and initiates it by activating the pump trigger 7. After a delay time of six hours, the pump conveys 475 µl of active substance within a period of about 90 minutes. The pump used for the output characteristic shown in FIG. 4 has the structure illustrated in FIG. 1. A commercially available Na polyacrylate hydrogel from BASF which has a particle size of (650±50) µm is used an actuator material 2.

Figure 5:
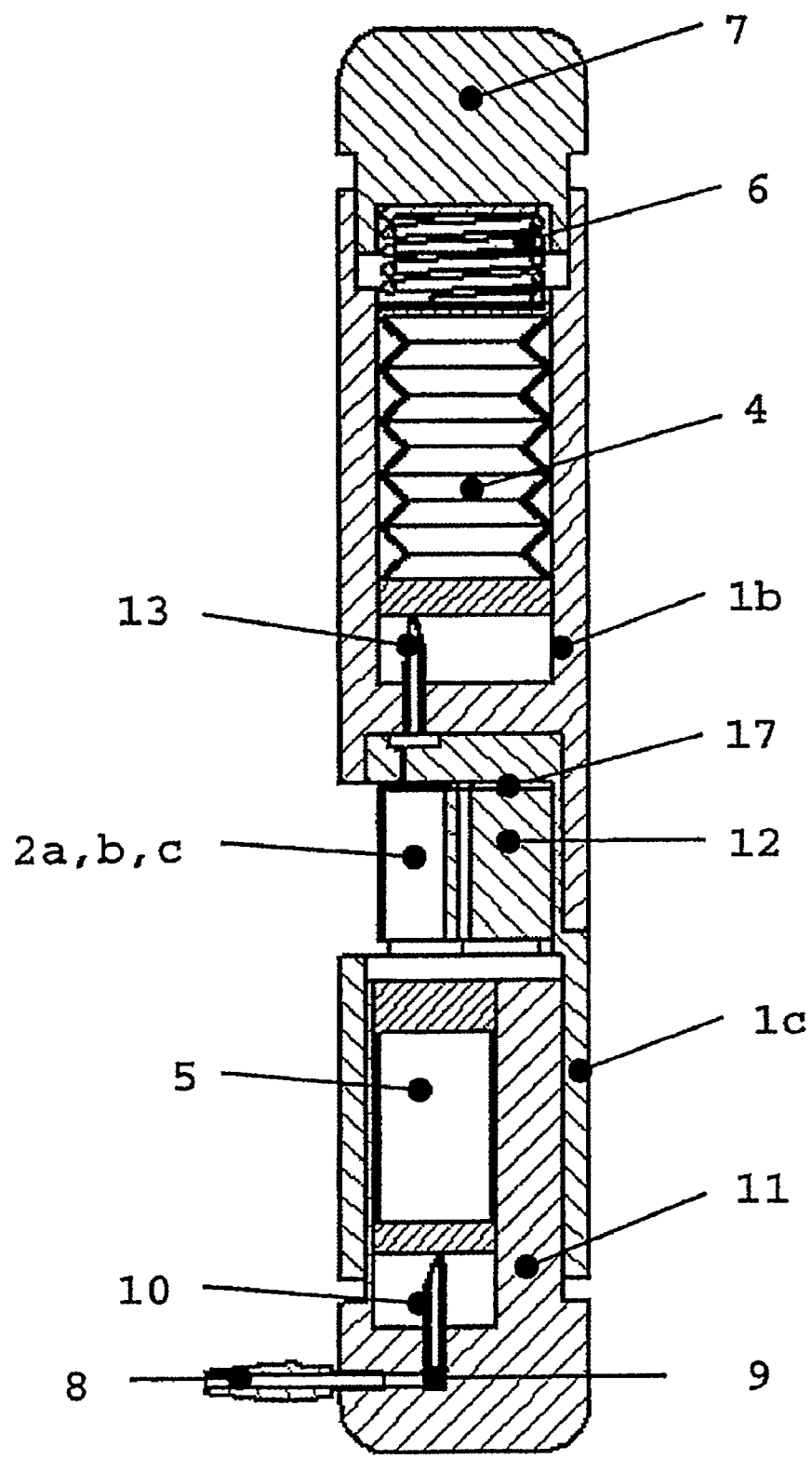
FIG. 5 shows an automatic pump or delivery device for continuous conveying whereby a defined amount of active substance is output per unit of time over a predetermined, adjustable period.

FIG. 5 illustrates pumps designed for continuous conveying at a defined delivery rate of active substance per unit of time over a defined, adjustable period.

The pump firstly has the same main components as the device depicted in FIG. 1, but without the time delay unit, since the latter is not needed for the application or use now being described. It is initiated by actuating the pump trigger 7, the flow of force generated by the user being led via the fully compressed pretensioning spring 6 onto the swelling agent reservoir 4 so that the force needed to pierce the actuator-side covering of the swelling agent reservoir 4 with the pin 13 is exceeded. The swelling agent can now pass through the piercing needle 13 to the actuator 2. The position-independent delivery of the swelling agent is again ensured by the pretensioning device 6 by means of hydrostatic overpressure.

Figure 5A:
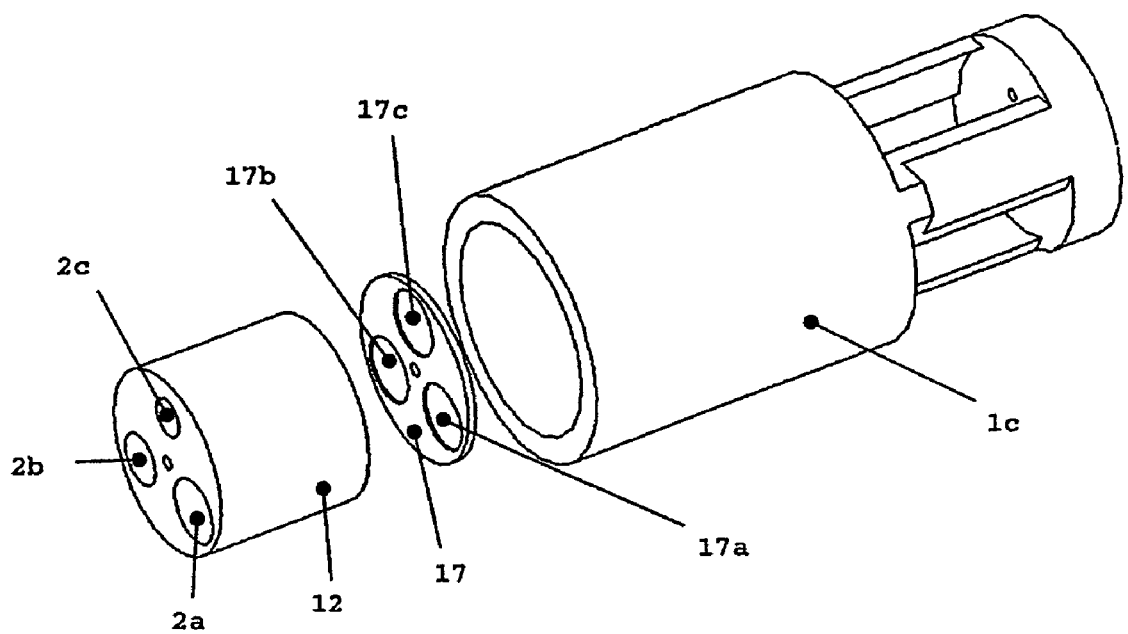
FIG. 5a shows a selector system for the automatic pump according to FIG. 5.

However, the swelling agent first has to pass the selector disk for the effective delivery cross section 17. In FIG. 5, the element 17 has three concentrically arranged areas with different delivery cross sections 17a, b, c (see also FIG. 5a). Since the selector disk 17 is mounted rotatably, the user can choose a suitable delivery cross section and thus fix the available quantity of swelling agent per unit of time. In this way he is able to fix the output rate of the pump, in other words how much active substance is to be conveyed per unit of time.

The time-dosed swelling agent now reaches the selector disk 12 which, for example, is provided with three function bores placed according to the concentric arrangement of the delivery cross sections of the element 17. In these function bores there are, for example, three different actuator segments 2a, 2b, 2c (see FIG. 5a) which can contain both a different actuator material composition and also different filled quantities. By suitable choice of the actuator 2a, b, c to be activated, it is possible to adjust, inter alia, the maximum conveyable total volume via the actuator effective filled quantity of actuator material. Moreover, precision adjustment of the actuator dynamics etc., is possible. In principle, by using the different pre-set characteristic curve adjustment possibilities in the selector disk system and their combinations, it is possible to achieve the same effect of a continuous conveying at a defined active substance delivery rate per unit of time over a defined, adjustable period. The selector system too can be designed differently than the example discussed here.

The swelling agent time-dosed via the selector element 17 now activates the actuator segment chosen with selector disk 12, for example 2a. This segment now presses on the likewise concentrically arranged active substance reservoir 5 and presses the latter until pierced on the pin 10. The pin 10 now opens the hitherto sterile active substance reservoir 5 and allows active substance to flow through the active substance outlet 8. The remaining actuator stroke drives the active substance out to the quantity predetermined by actuator material or actuator filler.

Figure 6:
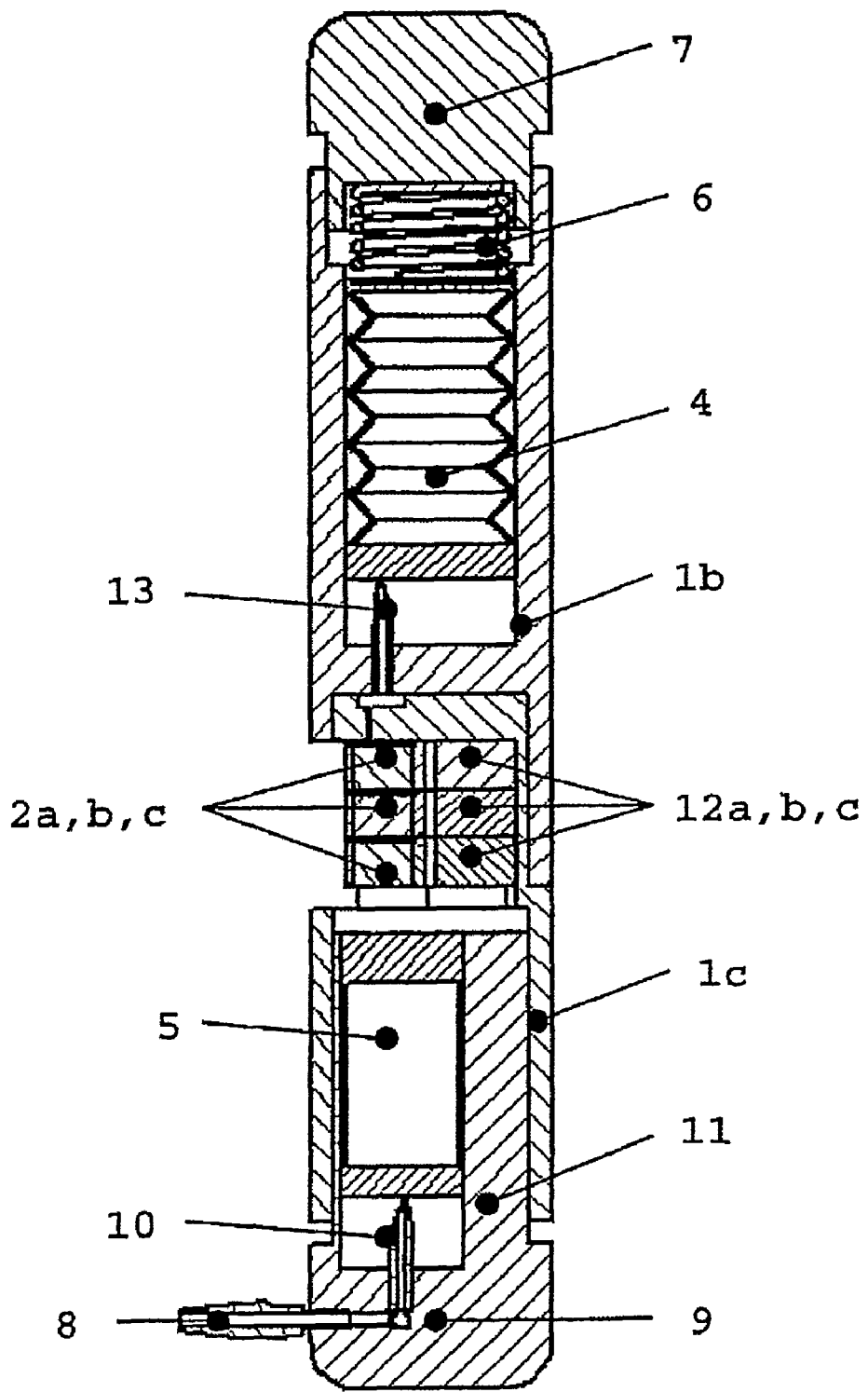
FIG. 6 shows an automatic pump with a mechanical time delay mechanism and mechanical selection of the output characteristic curve (pulsatile action pump)

Through a corresponding combination of several selector elements, it is possible to obtain an automatically conveying pump with adjustable, pulsatile output characteristics. Such a pump is shown by way of example in FIG. 6.

Figure 6A:
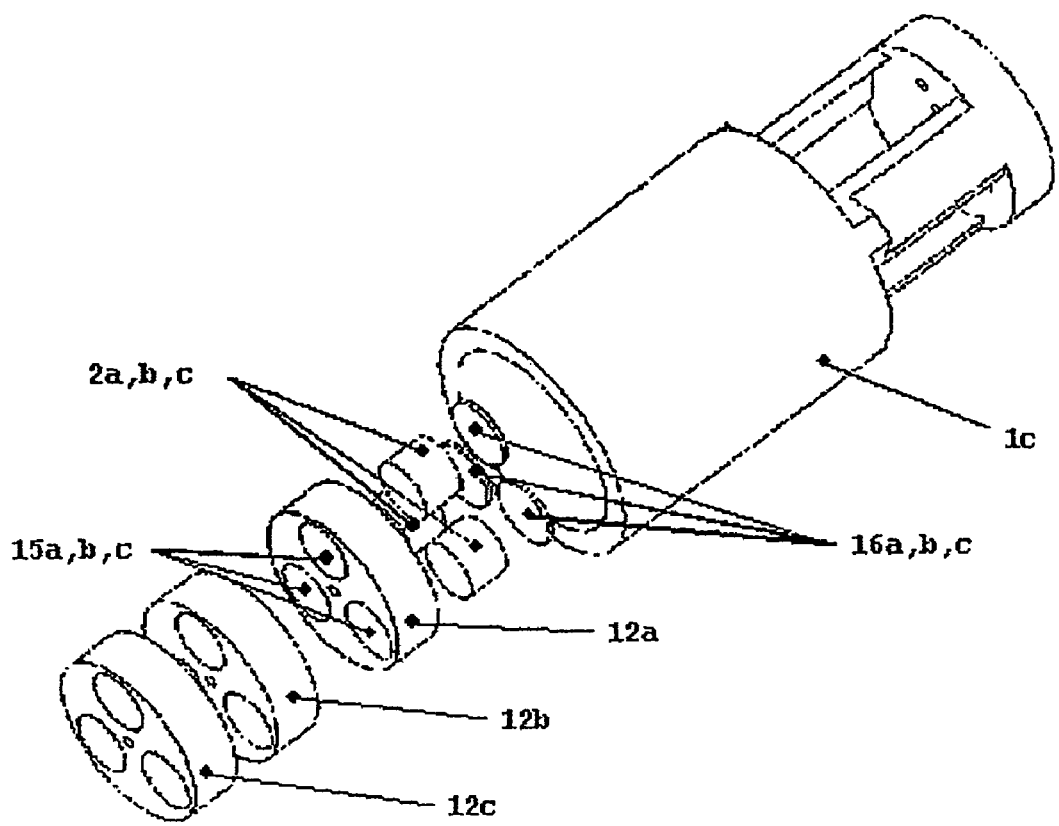
FIG. 6a shows the structural assembly for mechanical programming of the pump according to FIG. 6.

The function sequence is initially the same as for the configuration described according to FIG. 5. After initiation of the flow of swelling agent, the swelling agent has to pass through a defined delivery cross section which again can be designed as a selector disk or, as is shown in FIG. 6a, in the form of separating membranes 16a, b, c as a component of the selector disk 12a. Thereafter, the swelling agent reaches the actuator segment 2a, b or c selected with the selector disk 12a and now begins to swell. The leading edge of the swelling agent passes through the selected actuator segment of the selector disk 12a completely and now reaches the actuator segment which has been switched on by the selector disk 12b and which may have other time-related actuator properties than 12a. The same sequence applies for selector disk 12c.

By means of the respective actuator stroke, the downstream actuator segments are forced out of their position in the selector disks. However, this is not critical because only the composition of individual conveying sections and their time course is fixed by selector disks 12a, b, c. In addition to actuator material, the function bores 15a, b or c of the selector disks 12 can also be non-active in actuator terms, but contain material furthering the actuator stroke and the leading edge of the swelling agent. This is relevant above all for interruptions in conveying.

The resulting, time-defined actuator stroke now opens the active substance reservoir 5 in the form already shown in FIG. 5 and drives the active substance in pulsatile form through the active substance outlet 8 from the pump.

This mechanically programmable pump embodiment can also be based exclusively or in combination on the other possibilities already discussed for influencing the pump (or delivery) characteristic curve.

While exemplary embodiments, including preferred embodiments, of the present invention and its use have been described herein, it is contemplated that various modifications could be made without deviating from the spirit of the present invention. Accordingly, it is intended that the scope of the present invention be dictated by the appended claims.

The invention claimed is:

1. An automatic conveyor for conveying a medium, the conveyor having an adjustable output characteristic, wherein by operation of a suitable swelling agent an actuator based on at least one swellable polymer network is activated and triggers an automatic chain of action comprising at least one of (a) a delay time from the user initiating the conveyor to the start of the conveying, (b) a period of time within which the medium is actually conveyed, (c) a characteristic curve during conveying, (d) a volume of medium to be conveyed per unit of time, and (e) a total volume of medium to be conveyed, wherein at least one of the delay time, the period of time, the characteristic curve, the volume and the total volume can be adjusted by the user, and wherein the characteristic curve during conveying is adjustable by selectively arranging one or more of a number of serially arranged selector elements, each of said elements having at least one function bore.

2. The automatic conveyor according to claim 1, wherein said selector elements comprise selector disks.

3. The automatic conveyor according to claim 1, wherein said selector elements each have concentrically arranged function bores.

4. The automatic conveyor according to claim 3, wherein said selective arranging comprises selectively aligning said bores relative to each other.

5. The automatic conveyor according to claim 1, wherein said conveying is pulsatile conveying.

6. The automatic conveyor as claimed in claim 1, wherein the actuator comprises actuator segments, and wherein the serially arranged selector elements interconnect actuator segments having one of different material basis, microscopic/macroscopic structure and filling quantity.

7. The automatic conveyor as claimed in claim 1, wherein the serially arranged selector elements contain segments with materials couplable into an actuator force flow, said materials not actuator active and serving the purpose of interrupting conveying and simply forwarding the actuator forces and the swelling agent.

8. The automatic conveyor as claimed in claim 1, wherein the serially arranged selector elements contain segments of different swelling agent delivery line cross sections with defined swelling agent throughput amounts per unit of time.

9. The automatic conveyor as claimed in claim 1, wherein the serially arranged selector elements contain segments made of materials with chronologically defined dissolution properties in the actuator swelling agent.

10. The automatic conveyor as claimed in claim 1, wherein the serially arranged selector elements contain segments of different cross sections which enable hydraulically active stepping-up and stepping-down mechanisms.

11. The automatic conveyor according to claim 1, wherein the characteristic curve is based on one of continuous or pulsatile conveying.

12. The automatic conveyor as claimed in claim 1, wherein suitable actuator materials are polymer networks readily swellable in aqueous solutions.

13. The automatic conveyor as claimed in claim 1, wherein the swelling agent is one of water and aqueous solutions.

14. The automatic conveyor as claimed in claim 1, wherein the actuator can be returned to an initial state through action of suitable environmental parameters and can thus be reused.

15. A delivery device for delivering a substance, the delivery device having an adjustable output, wherein by operation of a suitable swelling agent an actuator triggers an automatic action comprising at least one of (a) a delay time from a user beginning to operate the device to the start of the delivery of the substance, (b) a period of time within which the substance is actually delivered, (c) a characteristic curve during delivery, (d) a volume of substance to be delivered per unit of time, and (e) a total volume of substance to be delivered, wherein at least one of the delay time, the period of time, the characteristic curve, the volume and the total volume can be adjusted by the user, and further comprising a number of serially arranged selector elements, wherein the characteristic curve is adjustable by selectively arranging said selector elements.

16. The automatic conveyor as claimed in claim 15, wherein the delay time is adjusted by varying an idling travel of the hydrogel actuator.

17. The automatic conveyor as claimed in claim 15, wherein a conveying rate or the amount conveyed per unit of time is selectable by varying at least one of the effective cross section of a swelling agent delivery line and the amount of swelling agent delivered per unit of time from the swelling agent delivery line to the actuator.

18. The automatic conveyor according to claim 17, wherein the conveying rate or the amount conveyed per unit of time are during substantially continuous conveying.

19. The automatic conveyor as claimed in claim 15, wherein the conveying rate or the amount conveyed per unit of time by the conveying device is adjustable by selecting an actuator material.

20. The automatic conveyor according to claim 19, wherein the conveying rate or the amount conveyed per unit of time are during substantially continuous conveying.

21. The automatic conveyor as claimed in claim 15, wherein the period of time within which the medium is actually conveyed is adjustable by selecting at least one of an actuator material and the a volume of actuator material.

22. The automatic conveyor as claimed in claim 15, wherein the total volume of medium to be conveyed is adjustable by one of setting the amount of swelling agent available as a whole and/or the amount of swellable actuator material available as a whole.

23. The automatic conveyor as claimed in claim 15, wherein delivery of the swelling agent to the actuator is independent of the position of the automatic conveyor.

24. The automatic conveyor as claimed in claim 23, wherein delivery of the swelling agent to the actuator is independent of the position of the automatic conveyor because a reservoir containing the swelling agent reservoir is acted upon by a hydrostatic overpressure.

25. The automatic conveyor as claimed in claim 23, wherein delivery of the swelling agent to the actuator is independent of the position of the automatic conveyor because the swelling agent is delivered from a reservoir to the actuator through a swelling agent conducting material.

26. The automatic conveyor as claimed in claim 25, wherein delivery of the swelling agent to the actuator is independent of the position of the automatic conveyor because the swelling agent is delivered from a reservoir to the actuator through a swelling agent conducting material as a result of capillary forces.

27. The automatic conveyor as claimed in claim 15, wherein the idling travel needed for realizing the time delay is reduced by the application of a counterforce.

28. The automatic conveyor as claimed in claim 27, wherein the counterforce is provided by a friction pairing.

29. The automatic conveyor as claimed in claim 15, wherein an active substance reservoir is opened, just before the start of a conveying process, by the actuator pressing the active substance reservoir onto an opening mechanism.

30. The automatic conveyor as claimed in claim 12, wherein said polymer networks comprise superabsorbers.

31. The automatic conveyor as claimed in claim 12, wherein said polymer networks comprise polyacrylates.

32. The automatic conveyor as claimed in claim 14, wherein suitable actuator materials are temperature-sensitive swellable polymer networks with discontinuous phase transition behavior, in particular with lower critical solution characteristics.

33. The automatic conveyor as claimed in claim 14, wherein the actuator-resetting environmental parameter is temperature.

34. The automatic conveyor as claimed in claim 33, wherein the actuator-resetting environmental parameter is temperature, applied by insertion into boiling water or steam.

* * * * *